US008053207B1

(12) United States Patent
Lamango

(10) Patent No.: US 8,053,207 B1
(45) Date of Patent: Nov. 8, 2011

(54) CANCER DIAGNOSIS BY MEASURING POLYISOPRENYLATED METHYLATED PROTEIN METHYL ESTERASE ACTIVITY

(75) Inventor: Nazarius Saah Lamango, Tallahassee, FL (US)

(73) Assignee: Florida Agricultural and Mechanical University, Tallahassee, FL (US)

( * ) Notice: Subject to any disclaimer, the term of this patent is extended or adjusted under 35 U.S.C. 154(b) by 0 days.

(21) Appl. No.: 13/012,942

(22) Filed: Jan. 25, 2011

(51) Int. Cl.
*C12Q 1/44* (2006.01)
(52) U.S. Cl. ........................................................ 435/19
(58) Field of Classification Search ..................... 435/19
See application file for complete search history.

(56) References Cited

U.S. PATENT DOCUMENTS

| | | | |
|---|---|---|---|
| 5,202,456 A | 4/1993 | Rando | |
| 5,574,025 A | 11/1996 | Anthony | |
| 5,705,528 A | 1/1998 | Kloog | |
| 6,372,793 B1 | 4/2002 | Lamango et al. | |
| 7,897,604 B2 * | 3/2011 | Lamango | 514/252.13 |

OTHER PUBLICATIONS

Perez-Sala et al., "Prenylated protein methyltransferases do not distinguish between farnesylated and geranylgeranylated substrates", Biochem J. 284:835-840 (1992).
Regazzi et al., "Prenylcysteine analogs mimicking the C-terminus of GTP-binding proteins stimulate exocytosis from permeabilized HIT-T15 cells: comparison with the effect of Rab3AL peptide", BBA 1268:269-278 (1995).
Roskoski, Jr., "Protein prenylation: a pivotal posttranslational process", BBRC 303:1-7 (2003).
Sinensky, "Recent advances in the study of prenylated proteins", BBA 1484:93-106 (2000).
Muhlig-Versen et al., "Loss of Swiss Cheese/Neuropathy Target Esterase Activity Causes Disruption of Phosphatidylcholine Homeostasis and Neuronal and Glial Death in Adult *Drosophila*", J Neurosci 25(11):2865-2873 (2005).
Morris et al., "Physiological Regulation of G Protein-Linked Signaling", Physio Rev 79(4):1373-1429 (1999).
Winter-Vann et al., "A small-molecule inhibitor of isoprenylcysteine carboxyl methyltransferase with antitumor activity in cancer cells", PNAS 102(12):4336-4341, 2005.
Lutz et al. "Feedback Inhibition of Polyisoprenyl Pyrophosphate Synthesis from Mevalonate in Vitro", J Bio Chem 267 (12):7983-7986 (1992).
Sinensky et al., "Functional aspects of polyisoprenoid protein substituents: roles in protein-protein interaction and trafficking", BBA 1529:203-209 (2000).
Sharar et al., "Extrapyramidal Parkinsonism Complicating Acute Organophosphate Insecticide Poisoning", Pediatric Neur 33(4):378-382 (2005).
Khosravi-Far et al., "Ras (CXXX) and Rab (CC/CXC) Prenylation Signal Sequences Are Unique and Functionally Distinct", J Bio Chem 267(34):24363-24368 (1992).
Ma et al., "Mechanistic Studies on Human Platelet Isoprenylated Protein Methyltransferase: Farnesylcysteine Analogs Block Platelet Aggregation without Inhibiting the Methyltransferase", Biochemistry 33:5414-5420 (1994).
Muller-Vahl et al., "Transient Severe Parkinsonism After Acute Organophosphate Poisoning", J Neurol Neurosurg Psychiatry 66:253-254 (1999).
Myung et al., "Role of Isoprenoid Lipids on the Heterotrimeric G Protein Gamma Subunit in Determining Effector Activiation", J Biol Chem 274(23):16595-16603 (1999).
Pereira-Leal, et al., "Prenylation of Rab GTPases: molecular mechanisms and involvement in genetic disease", FEBS 498:197-200 (2001).
Anderegg, at al., "Structure of *Saccharomyces cerevisiae* Mating Hormone A-Factor. Identification of S-Farnesyl Cysteine as a Structural Component", J Bio Chem, 263:18236-18240 (1988).
Anderson, et al., "Purification, functional Reconstitution and Characterization of the *Saccharomyces cerevisiae* Isoprenylcysteine Carboxylmethyltransferase", J Bio Chem 280:7336-7345 (2005).
Ascherio, et al., "Pesticide Exposure and Risk for Parkinson's Disease", Ann Neurol 60:197-203 (2006).
Becker, et al., "Synthesis and Structure-Activity Relationships of Beta and Alpha Piperidine Sulfone Hydroxamic Acid Matrix Metalloproteinase Inhibitors With Oral Antitumor Efficacy", J Med Chem 48:6713-6730 (2005).
Bergo, et al., "Isoprenylcysteine Carboxyl Methyltransferase Deficiency in Mice", J Bio Chem 276:5841-5845 (2001).
Bifulco, "Rose of the Isoprenoid Pathway in ras Transforming Activity, Cytoskeleton Organization, Cell Proliferation and Apoptosis", Life Sciences 771740-1749 (2005).
Calero, et al., "*Saccharomyces cerevisiae* Pra1p/Yip3p Interacts with Yip1p and Rab Proteins", Biochem Biophys Res Commun 290:676-381 (2002).
Chen, et al., "G Protein Beta2 Subunit Interacts Directly with Neuropathy Target Esterase and Regulates its Activity", Intl J Biochem & Cell Biology 39:124-132 (2007).
Capdevila et al., "Pancreatic Exocrine Secretion is Blocked by Inhibitors of Methylation", Arch Biochem Biophys 345:47-55 (1997).
Cohen et al., "Inhibitors of Prenylation of Ras and Other G-Proteins and Their Application as Therapeutics", Biochem Pharma 60:1061-1068 (2000).
Costa, "Current Issues in Organophosphate Toxicology", Clin Chem Acta 366:1-13 (2006).
Dietrich, et al., "Isoprenylation of the G Protein Gamma Subunit is Both Necessary and Sufficient for Beta Gamma Dimmer-mediated Stimulation of Phospholipase", C Biochem 35:15174-15182 (1996).
Ding, et al., "Farnesyt-L-Cysteine Analogs Can Inhibit of Initiate Superoxide Release by Human Neutrophils", J Biol Chem 269:16837-16844 (1994).
Dolence et al., "A mechanism for posttranslational modifications of proteins by yeast protein farnesyltransferase", Proc Natl Acad Sci 92:5008-5011 (May 1995). Ehrhardt et al., "Ras and relatives—job sharing and networking keep an old family together", Exp Hematology 30:1089-1106 (2002).
Glynn, Paul, "Neuropathy target esterase and phospholipid deacylation", BBA 1736:87-93 (2005).
Gosser et al., "C-terminal binding domain of Rho GDP-dissociation inhibitor directs N-terminal inhibitory peptide to GTPases", Nature 387:814-819 (Jun. 19, 1997).

(Continued)

*Primary Examiner* — Maryam Monshipouri
(74) *Attorney, Agent, or Firm* — Parks IP Law LLC; Collen A. Beard, Esq.

(57) ABSTRACT

Methods for cancer diagnosis and treatment; in particular, methods for diagnosis and treatment of triple negative breast cancer by measuring the activity of PMPMEase.

20 Claims, 3 Drawing Sheets

OTHER PUBLICATIONS

Kloog et al., "Prenyl-binding domains: potential targets for Ras inhibitors and anti-cancer drugs", Seminars in Cancer Bio 14:253-261 (2004).

Lamango et al., "Quantification of S-Adenosylmethionine-Induced Tremors: A Possible Tremor Model for Parkinson's Disease" Pharm Biochem and Behavior 65(3):523-529 (2000).

Lebowitz et al, "Farnesyltransferase Inhibitors Alter the Prenylation and Growth-stimulating Function of RhoB", J Bio Chem 272(25):15591-15594 (Jun. 20, 1997).

Lamango et al., "Liver Prenylated Methylated Protein Methyl Esterase is an Organophosphate-Sensitive Enzyme", J Biochem Molecular Toxicology 19(5):347-357 (2005).

Marom et al., "Selective Inhibition of Ras-dependent Cell Growth by Farnesylthiosalisylic Acid", J Bio Chem 270 (38):22263-22270 (Sep. 22, 1995).

Martincic et al., "Isolation and Characterization of a Dual Prenylated Rab and VAMP2 Receptor", J Bio Chem 272 (43):26991-26998 (Oct. 24, 1997).

McTaggart, S.J., "Isoprenylated proteins", Cell Mol Life Sci 62:255-267 (2006).

Seabra, et al. "Rab GTPases, Intercellular Traffic and Disease", Trends in Mol Med 8(1):23-30 (2002).

Seymore, L., "Novel anti-cancer agents in development: exciting prospects and new challenges", Cancer Treatment Rev 25:301-312 (1999).

Shields et al., "Understanding Ras: 'it ain't over 'til it's over'", Trends Cell Bio 10:147-154 (Apr. 2000).

Parish et al., "Isoprenylation/Methylation of Proteins Enhances Membrane Association by a Hydrophobic Mechanism" Biochem 35(26):8473-8477 (1996).

* cited by examiner

CANCER DIAGNOSIS BY MEASURING POLYISOPRENYLATED METHYLATED PROTEIN METHYL ESTERASE ACTIVITY

STATEMENT REGARDING FEDERALLY SPONSORED RESEARCH OR DEVELOPMENT

This invention was made with government support under NIH/NIGMS/SCORE grant GM 08111-35 and Pharmaceutical Research Center NIH/NCRR grant G12 RR0 3020. The government has certain rights in the invention.

BACKGROUND OF THE INVENTION

It has been discovered that the activity of a particular enzyme, polyisoprenylated methylated protein methyl esterase (PMPMEase which is also known as human carboxylesterase 1 or hCE1), is elevated in certain cancers, particularly in breast cancer. The present invention is methods for the diagnosis and treatment of cancer, particularly breast cancer, by measuring the activity of the enzyme PMPMEase.

Breast cancer is not one disease but several different diseases. Three types of breast cancer are estrogen receptor (ER)-positive breast cancer, progesterone receptor (PR)-positive breast cancer (together termed hormone receptor positive breast cancer), and human epidermal growth factor receptor 2 (HER2)-positive breast cancer (triple positive breast cancer refers to the presence of ER, PR, and HER2 receptors). These subtypes of breast cancer are generally diagnosed based upon the presence, or lack of, these three receptors. In addition, the most successful treatments for breast cancer target these receptors. Another type of breast cancer is called triple negative breast cancer, since none of these three receptors are found in the offending tumor. Because of its triple negative status, triple negative tumors generally do not respond to receptor targeted treatments. Depending on the stage of its diagnosis, triple negative breast cancer can be particularly aggressive, and more likely to recur than other subtypes of breast cancer. Although it cannot be treated with receptor targeted treatments it is commonly receptive to chemotherapy. The lack of targets for treating triple negative breast cancer implies that more research needs to be pursued to find what drives this form of cancer as well as other cancers of unknown etiologies.

Proper diagnosis of the type of breast cancer is essential for proper treatment.

Protein polyisoprenylation and subsequent methylation are essential modifications on a significant proportion of eukaryotic proteins. The modifications are a series of post-translational modifications involving motifs such as -CAAX wherein C is cysteine, A is any aliphatic amino acid, and X is any amino acid whose nature specifies either farnesylation or geranylgeranylation. The modifications include polyisoprenylation of the cysteine of the -CAAX motif (on the sulfur), proteolysis of the carboxyl-terminal three amino acids (AAX), and methylation of the carboxyl group of the cysteine. In the polyisoprenylation step, a 15 carbon (trans, trans-farnesyl) or 20 carbon (all trans-geranylgeranyl)hydrocarbon group is covalently added to the protein.

The only reversible step in the process is the last step, methylation. Two enzymes mediate this final state of polyisoprenylated proteins. Polyisoprenylated protein methyl transferase (PPMTase), also known as isoprenyl carboxylmethyl transferase (ICMT), transfers a methyl group from S-adenosyl-L-methionine (SAM) to the C-terminal —COO⁻ to form the methylated polyisoprenylated protein. PPMTase is essential to the developing embryo; knockout mice lacking PPMTase activity do not survive through mid-gestation. The second of the two enzymes is polyisoprenylated methylated protein methyl esterase (PMPMEase), which hydrolyzes the methyl esters of polyisoprenylated proteins to form the original proteins with free —COO⁻ groups.

PPMTase and PMPMEase counterbalance the effects of each other. It is conceivable that the methylated and demethylated forms of prenylated proteins may be variously preferred for functional interactions by different protein targets, thus rendering PPMTase and PMPMEase very important moderators of polyisoprenylated protein function. Accordingly, manipulation of these enzymes should render significant effects on many cellular functions.

PMPMEase, through its possible regulation of the functions of various types of polyisoprenylated proteins, may exert profound effects on various intracellular events and consequently on animal physiology. Proteins such as the G-gamma subunits of heterotrimeric G-proteins of the G-protein coupled receptors, nuclear lamins, and guanine nucleotide-binding proteins such as Ras are polyisoprenylated and undergo methylation. These proteins mediate processes ranging from neurotransmitter signaling, cytoskeletal and intracellular transportation functions, cell proliferation, differentiation, and apoptosis. It could be inferred from this that aberrant levels of PMPMEase activity would be expressed through disease states such as cancers, neurodegenerative, and neuropsychiatric disorders. In fact, hyperactivity of monomeric G-proteins is implicated in an estimated 30% of cancers. Ghobrial IM, et al., Hematol. Oncol. Clin North Am. 2002, 16(5):1065-1088.

PMPMEase is inhibited by millimolar concentrations of the anticancer drugs tamoxifen and cyclophosphamide as well as by micromolar concentrations of the chemopreventive compound curcumin and polyunsaturated fatty acids such as arachidonic acid (AA). Prostaglandin (PG) $A_2$ was 63-fold less potent than AA while $PGE_2$ did not inhibit PMPMEase at 1 mM. AA's effects on cell death coupled with the expression of COX-2 in various tumors and tumor cell lines may imply that COX-2 converts AA into PGs, thereby destroying AA's ability to effectively inhibit PMPMEase and regulate cell growth. These results also show that balanced PMPMEase activity may be critical for normal cell viability.

It is an object of the invention to provide a method for detecting cancer, particularly breast cancer. The method involves measuring the activity of the enzyme PMPMEase.

SUMMARY OF THE INVENTION

The present invention is methods for the diagnosis, prediction, and treatment of cancer, particularly breast cancer, based upon the activity of the enzyme PMPMEase.

PMPMEase activity is elevated in cancerous tissue compared to surrounding non cancerous tissue. Accordingly, an increase in PMPMEase activity is a marker for the presence of cancer, or a predisposition to cancer. Measurement of PMPMEase activity can therefore be the basis for cancer diagnosis, decisions on appropriate cancer treatment, awareness of a predisposition to cancer and potential cancer prevention, and monitoring of cancer therapy.

In one embodiment, the invention is a method of cancer diagnosis or prediction (together termed "detection") including the steps 1) gathering a biological sample from a subject and 2) assaying the biological sample for PMPMEase activity. In a third step the PMPMEase activity in the biological sample is compared to PMPMEase activity in a control biological sample. In preferred embodiments the biological sample is from a breast tumor.

DETAILED DESCRIPTION OF THE INVENTION

Figure 1:
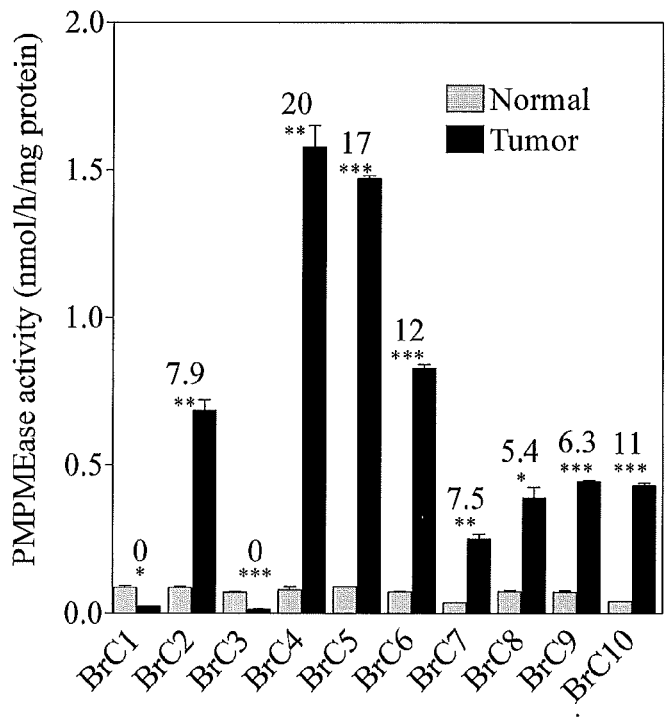
FIG. 1 is a chart showing PMPMEase activity in nmol/h/mg protein. Tumor samples are shown as solid black bars with corresponding normal tissue as gray bars. Each bar represents the mean±SEM, N=3. The number above each pair of bars represents the fold increase in the activity in the tumor sample over that of the normal adjacent tissue. The significance between the tumors and adjacent normal tissues were calculated using paired t-tests and *,  and * denote P-values equal to or less than 0.05, 0.01 and 0.001, respectively.

PMPMEase activity is elevated in cancerous tissue compared to surrounding non cancerous tissue. Accordingly, an increase in PMPMEase activity is a marker for the presence of cancer, or a predisposition to cancer.

In one embodiment, the invention is a method of cancer detection including the steps 1) gathering a biological sample from a subject and 2) assaying the biological sample for PMPMEase activity. In a third step the PMPMEase activity in the biological sample is compared to PMPMEase activity in a control biological sample.

Cancer as used herein means the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. Cancers include, but are not limited to breast cancer, lung cancer, bronchus cancer, colorectal cancer, prostate cancer, pancreas cancer, stomach cancer, ovarian cancer, urinary bladder cancer, brain or central nervous system cancer, peripheral nervous system cancer, esophageal cancer, cervical cancer, a melanoma, uterine or endometrial cancer, cancer of the oral cavity or pharynx, liver cancer, kidney cancer, testis cancer, biliary tract cancer, small bowel or appendix cancer, salivary gland cancer, thyroid gland cancer, adrenal gland cancer, osteosarcoma, and a chondrosarcoma. While the invention is particularly shown herein as applicable for detection of breast cancer it is applicable to other cancers as well. In particular, it is likely that lung, prostate, liver, colon, kidney, and brain cancers also have elevated levels of PMPMEase activity.

In another embodiment the invention is a method of preventing development or further development of cancer. If a subject is found to have elevated levels of PMPMEase activity, indicating a predisposition towards or presence of cancer, measures can be taken to prevent further development of the cancer. An appropriate cancer therapy depends upon the type and extent of the cancer and can be selected from chemotherapy, radiation therapy, surgery, antihormone therapy, receptor-targeted therapy, and immunotherapy. Other therapies include changes in diet and exercise. For example, in those cases where the PMPMEase activities are elevated, the consumption of foods rich in natural PMPMEase inhibitors such as polyunsaturated free fatty acids and curcumin may be recommended as alternative remedies or for prevention of relapse. Specifically designed high affinity inhibitors of PMPMEase appropriately developed as drugs will be more suitable for targeting cancers with elevated PMPMEase activities.

In a preferred embodiment, the method is specific for detection of triple negative breast cancer. PMPMEase has particularly high activity in triple negative breast cancer. This is a particularly striking result since triple negative breast cancer has heretofore been difficult to treat. Although chemotherapy is a treatment option for triple negative breast cancer, the lack of a specific drug target implies that response to therapy is less than for the hormone-driven breast cancers which have more specific targeted therapeutic options and consequently better prognoses.

In another embodiment the invention is a method of screening foods, drugs, and other active agents for their ability to prevent or treat cancer by measuring their effect on PMPMEase activity.

In still another embodiment, the invention is the development of inhibitors targeted towards the suppression of PMPMEase activity to the level found in normal tissues.

In another embodiment, the invention is useful for treatment monitoring-measuring PMPMEase levels as a treatment progresses to determine its effectiveness.

PMPMEase activity can be measured in a number of ways that will be understood by those skilled in the art. Generally, enzyme activity is measured by measuring either the consumption of a substrate or the production of a product over time. For example, the biological sample can be incubated with a known PMPMEase substrate for a period of time, after which time the sample is assayed for the known enzymatic product.

The first step in the method is to collect the biological sample. This can be done through means well known in the art, by removing a sample of cells from the subject, but can also be accomplished by using previously isolated cells, or by performing the enzyme assay in vivo. The biological sample could alternatively be non-cellular biological material, such as non-cellular fractions of blood, saliva, or urine that can be used to measure PMPMEase activity. Preferred biological samples include tissue biopsies, scrapes (e.g. buccal scrapes), whole blood, plasma, serum, urine, saliva, cell culture, or cerebrospinal fluids. All of these are referred to herein as the biological sample or cells unless otherwise noted.

Often a control biological sample will also be obtained from the subject. This is a sample of biological material representative of healthy, cancer-free cells, preferably cells or tissue obtained from the same location of the subject. A control sample can also refer to an established level of PMPMEase activity representative of the cancer-free cells, which has been previously established based on measurements from normal, cancer-free cells.

The biological sample and control sample may need to be processed prior to the assay for PMPMEase activity. For example, it may be desirable to weigh and sonicate, homogenize or lyse the cells or tissues in a suitable buffer of pH at around 7.4 prior to incubation with the substrate. After incubation of the tissue extract/sample at or about 37° C. for a suitable amount of time, the reaction can be stopped by introducing conditions that denature proteins such as by heating or preferably adding a reagent that denatures the enzyme. Such reagents include, but are not limited to methanol and ethanol. Reagents such as acids or bases that may cause the ester bonds to break would generally be unsuitable. After centrifuging the stopped reactions to remove particulate matter, the supernatant liquids can then be analyzed.

The general PMPMEase reaction is shown as:

BzGFCM

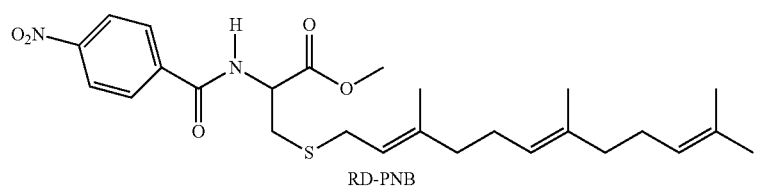
RD-PNB

A number of PMPMEase substrates can be used to assay PMPMEase activity. In order for PMPMEase to be selective for the substrate and to avoid interference from other esterases, $R_2$ is a polyisoprenyl group such as a trans, trans-farnesyl or all trans-geranylgeranyl group. Other hydrophobic groups can be used for $R_2$ with varying degrees of selectivity for PMPMEase. $R_3$ is naturally a methyl group as found in polyisoprenylated proteins and for the purposes of detecting the enzyme activity, a methyl as $R_3$ will serve the purpose although ethyl and other usually hydrophobic groups will still be functional. $R_1$ can be very diverse in chemical structure and application. For the purpose of sensitivity, groups that interact strongly with light such as fluorescent or chromophoric (light absorbing) groups will be most effective. The substrates can also be adapted for other detection methods such as radiolabeling.

A preferred substrate is L-N-(4-nitrobenzoyl)-S-trans, trans-farnesyl-cysteine methyl ester (RD-PNB). Other substrates that could be used are L-N-(2-nitrobenzoyl)-S-trans, trans-farnesyl-cysteine methyl ester, L-N-(3-nitrobenzoyl)-S-trans, trans-farnesyl-cysteine methyl ester, L-N-(benzoyl)-S-trans, trans-farnesyl-cysteine methyl ester, L-N-(hippuryl)-S-trans, trans-farnesyl-cysteine methyl ester or L-N-(benzoyl-glycyl)-S-trans, trans-farnesyl-cysteine methyl ester (BzGFCM) and their geranyl and geranylgeranyl analogs. The structures of BzGFCM and RD-PNB are shown below.

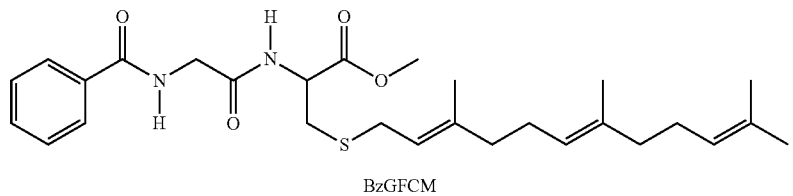
BzGFCM

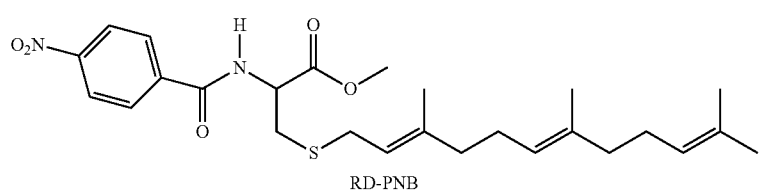
RD-PNB

Once the biological sample is obtained and processed, if desired, it is assayed for PMPMEase activity. The amount of PMPMEase activity in the tumor biological sample can be compared against the PMPMEase activity in normal control tissue. Preferably the difference between the increased level of PMPMEase activity in the biological sample and the level of PMPMEase activity in the control sample is statistically significant.

In one embodiment, the amount of product formed is determined using reversed-phase high performance liquid chromatography with ultraviolet detection (HPLC-UV). The amounts of product formed will then be computed with the aid of a standard plot of amount of product against ultraviolet absorption to determine the relative activities of PMPMEase in the biological samples in order to make a diagnosis.

Other means for measuring the product formation or substrate depletion include radioactively labeling the substrate. In such as a scenario, reversed-phase HPLC analysis with radiochromatographic detection or other chromatographic methods coupled with radioactivity detection methods can be used.

An increase in an enzyme's activity may be due to increased levels of the protein, a mutation that makes the protein more active (also called gain-of-function mutation to distinguish it from loss-of-function mutations that result in a less active protein), or the loss of a moderating factor such as a natural endogenous or exogenous inhibitor. Increased expression of enzyme can be monitored by quantifying the levels of messenger RNA (mRNA) using RT-PCR (less accurate) or levels of protein using ELISA and/or western blotting (WB) and/or immunohistochemistry (IH). ELISA, WB and IH—which involve the use of antibodies—can be jointly termed immunological methods and are more predictive of increased protein levels and/or activity than RT-PCR. Changes in protein activity that are due to mutations only but which do not affect gene regulation i.e. do not cause changes in mRNA and therefore protein synthesis cannot be detected by western blotting and ELISA. Loss of a moderating factor is also not detectable by WB and ELISA using antibodies directed at PMPMEase.

Changes in PMPMEase's activity due to any of the three factors above can be detected by the above discussed PMPMEase enzymatic assays. However, for some, perhaps a significant proportion of the cases, the increase in PMPMEase enzyme activity will be due to an increase in PMPMEase expression. Therefore, RT-PCR and the immunological methods for measuring increase in PMPMEase levels can also be used to predict increased PMPMEase activity. Because of the reasons stated above and the fact that proteins may be inactive due to denaturation and/or functional regulation, the true physiological impact of a protein can be most accurately evaluated using a functional assay of its activity.

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. In the examples, unless expressly stated otherwise, amounts and percentages are by weight, temperature is in degrees Celsius or is at ambient temperature, and pressure is at or near atmospheric.

Materials and Methods

Ten breast cancer tumor samples together with respective matching adjacent normal tissues were obtained from Proteo-Genex (Culver City, Calif.). The specimens were from ten Caucasian women ranging from age 44 to 77 years. The ER, HER2 and progesterone receptor status for three of the ten samples was known. The sample BrC5 was triple negative, BrC7 was positive for estrogen and progesterone receptors and negative for HER2, and BrC10 was positive for HER2 only. The tissues were collected and surgically excised by certified medical pathologists at ProteoGenex and snap-frozen in liquid nitrogen within 30 min of surgery. All the samples were of stage IIIA with histological diagnoses of infiltrating ductal carcinomas. The samples and their characteristics are listed in Table 1.

The TNM Classification of Malignant Tumours (TNM) is a cancer staging system that describes the extent of cancer in a patient's body. T describes the size of the tumor and whether it has invaded nearby tissue and ranges from 0 to 4, N describes the degree of spread to regional lymph nodes and ranges from 0 to 3, and M describes presence of metastasis and is either 0 (no metastasis) or 1 (metastasis beyond regional lymph nodes).

TABLE 1

| ID | Grade | TNM | ER/PR/HER2 status |
|---|---|---|---|
| BrC1 | G2 | T2N2M0 | unknown |
| BrC2 | G3 | T2N2M0 | unknown |
| BrC3 | G2 | T2N2M0 | unknown |
| BrC4 | G3 | T2N2M0 | unknown |
| BrC5 | G3 | T3N1M0 | Triple negative |
| BrC6 | G2-G3 | T2N2M0 | unknown |
| BrC7 | G2 | T2N2M0 | ER(+)/PR(+) |
| BrC8 | G2 | T2N2M0 | unknown |
| BrC9 | G3 | T3N1M0 | unknown |
| BrC10 | G3 | T2N2M0 | HER2 (+) |

The substrate L-N-(4-nitrobenzoyl)-S-trans,trans-farnesyl-cysteine methyl ester (RD-PNB) was synthesized as described in Lamango, N. S. et al. (2009) TOEIJ 2, 12-27(1). This substrate is an adaptation of the PMPMEase substrates described in Lamango, N. S. (2005) J Biochem Mol Toxicol 19, 347-357 and Oboh, O. T. et al. (2008) J Biochem Mol Toxicol 22, 51-62.

The frozen tumor and adjacent matching controls were weighed and sonicated in ice-cold 100 mM Tris-HCl buffer, pH 7.4 (5× mass of tissue). Aliquots of the homogenates (95 μL) were incubated with the RD-PNB substrate (1 mM) at 37° C. for 3 h. The reactions were stopped by the addition of 200 μL methanol. After chilling them at −20° C. for at least 5 min, they were centrifuged at 5000×g for 5 min and the supernatants analyzed by reversed-phase HPLC with UV-detection at 260 nm as described in Lamango, N. S. et al. (2009) *TOEIJ* 2, 12-27(1). The amount of product formed was determined using a calibration plot of HPLC UV-peak areas for known amounts of product standards. The total protein in the homogenates was determined using the bicinchoninic acid method.

Results

Figure 2:
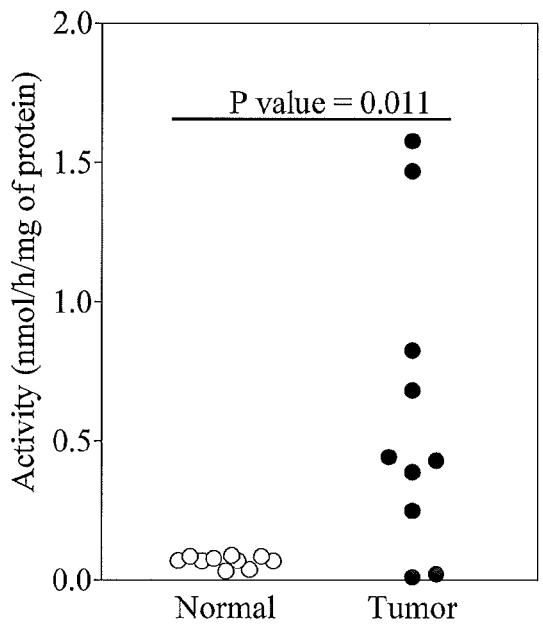
FIG. 2 is a chart of PMPMEase activity in nmol/h/mg protein for tumor and normal samples showing a P value of 0.011.
Figure 3:
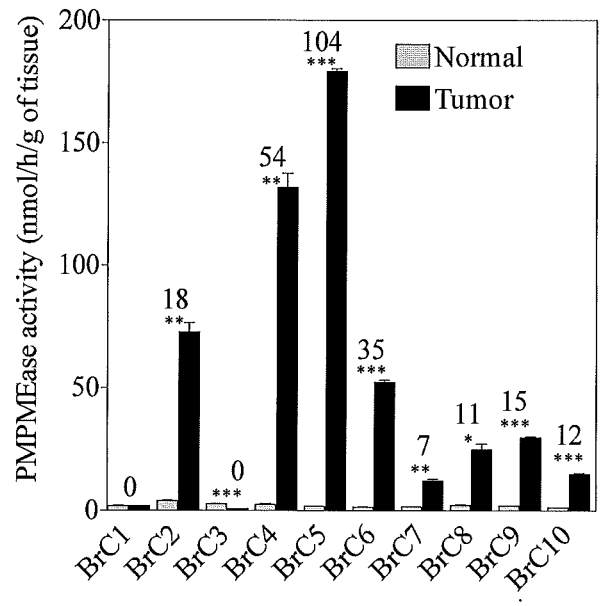
FIG. 3 is a chart showing PMPMEase activity in nmol/h/g of tissue fresh weight. Tumor samples are shown as solid black bars with corresponding normal tissue as gray bars. Each bar represents the mean±SEM, N=3. The number above each pair of bars represents the fold increase in the activity in the tumor sample over that of the normal adjacent tissue. The significance between the tumors and adjacent normal tissues were calculated using paired t-tests and *,  and * denote P-values equal to or less than 0.05, 0.01 and 0.001, respectively.
Figure 4:
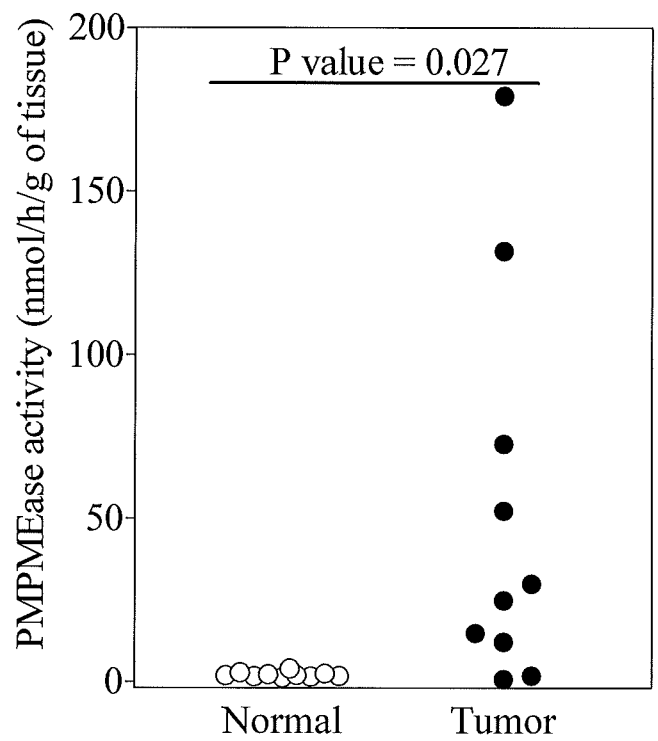
FIG. 4 is a chart of PMPMEase activity in mmol/h/g of tissue protein for tumor and normal samples showing a P value of 0.027.

FIGS. 1 and 2 illustrate PMPMEase activity as nmol/h/mg protein and FIGS. 3 and 4 show activity as nmol/h/g of tissue. Significantly higher enzymatic activities were detected in the cancer samples compared to the respective controls. As shown in FIGS. 1 and 2, the activities ranged from 0.03 to 0.09 nmol/h/mg of protein with a mean and standard deviation of 0.07±019 for the normal group compared to a range of 0.01 to 1.6 nmol/h/mg of protein (mean and standard deviation of 0.61±0.54) for the tumor samples. This reflects an 8.7-fold increase in total protein-based PMPMEase specific activity.

When the samples were analyzed based on the weighed mass of tissue rather than the total protein (FIGS. 3 and 4), even larger differences were observed between the normal and the cancer tissues. These ranged from 1.29 to 3.98 (mean of 2.13) nmol/h/g of tissue for the control group and 0.76 to 179 (mean of 52.0) nmol/h/g of tissue for the cancer tissue. This reflects a 24.4-fold increase in PMPMEase activity in the cancer over the control tissues. As shown in FIGS. 1 and 3, significant increases in PMPMEase activity were noted in 8 out of the 10 cases studied. Eliminating the two cases that showed no increased PMPMEase activities from the analysis reveal 11.3- and 31-fold increases for the protein based and tissue weight specific activities, respectively. The increase in PMPMEase activity in the tumor versus the respective control tissues ranged from 5.4- to 20-fold when measured in terms of protein and 7- to 104-fold when measured against tissue weight.

Specific Samples

BrC5, known to be triple negative, shows the most enhanced PMPMEase activity when based on the weighed mass of tissue (FIG. 3) and second highest when based on total protein. BrC7 (ER and PR positive) and BrC10 (HER2 positive) show much less increased PMPMEase activity.

Further Analysis of Triple Negative BrC5

Figure 5:
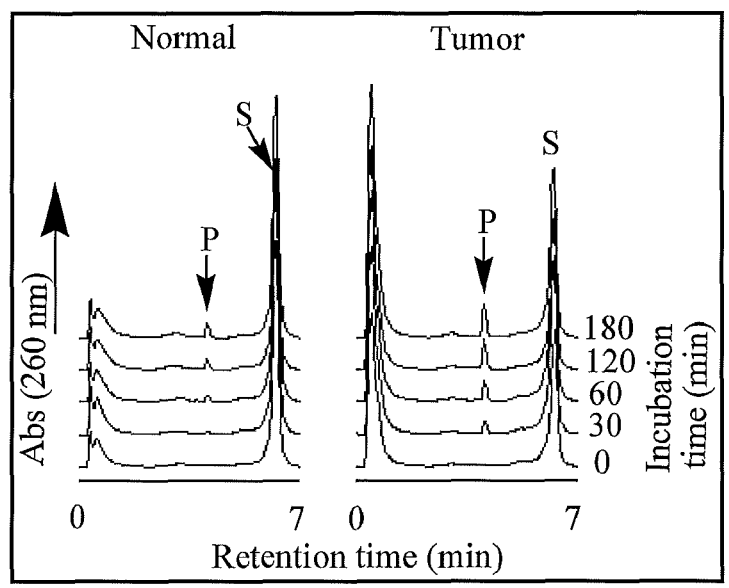
FIG. 5 shows product production and substrate depletion over time for normal and tumor tissue.
Figure 6:
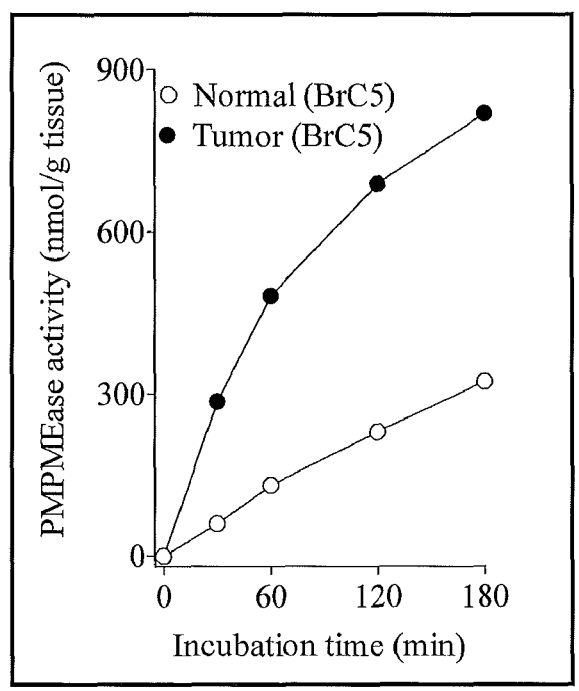
FIG. 6 charts the data shown in FIG. 5 as PMPMEase activity (nmol of product formed/g tissue) versus incubation time.

In a time-course analysis of substrate hydrolysis by BrC5 control and tumor tissues, 10 μL of homogenate was used instead of the 95 μL used in the initial screening of the samples. Briefly, 10 μL the homogenate was incubated with the RD-PNB substrate (1 mM) at 37° C. At the indicated time points, the reactions were stopped by the addition of 200 μL methanol. After chilling them at −20° C. for at least 5 min, they were centrifuged at 5000×g for 5 min and the supernatants analyzed by reversed-phase HPLC with UV-detection at 260 nm as described in Lamango, N. S. et al. (2009) *TOEIJ* 2, 12-27(1). The amounts of product formed were determined using a calibration plot of HPLC UV-peak areas for known amounts of product standards. As shown in FIGS. 5 and 6, the rate of formation of product was significantly higher in the tumor samples compared to the controls.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A method for detection of breast cancer in a biological sample comprising the step of assaying the biological sample for PMPMEase activity.

2. The method of claim 1 wherein PMPMEase activity is PMPMEase enzymatic activity or PMPMEase expression.

3. The method of claim 1 further comprising the step of comparing the PMPMEase activity in the biological sample to PMPMEase activity in a non-cancerous biological sample.

4. The method of claim 1 wherein the biological sample is from a breast tumor.

5. The method of claim 1 wherein the cancer is triple negative breast cancer.

6. The method of claim 2 wherein the expression of PMPMEase is determined by an immunological method.

7. The method of claim 2 wherein the expression of PMPMEase is determined by real time-polymerase chain reaction (RT-PCR).

8. The method of claim 1 wherein the assaying step comprises incubating the biological sample with a PMPMEase substrate and measuring a change in concentration of the substrate or a product known to be produced by PMPMEase from the substrate.

9. The method of claim 8 wherein the substrate or product concentration is compared against a standard curve.

10. The method of claim 8 wherein the substrate is L-N-(4-nitrobenzoyl)-S-trans,trans-farnesyl-cysteine methyl ester (RD-PNB).

11. A method for determining whether a breast tumor is triple negative type breast cancer comprising the steps of obtaining a biological sample of the tumor and assaying the sample for PMPMEase activity.

12. The method of claim 11 wherein PMPMEase activity is PMPMEase enzymatic activity or PMPMEase expression.

13. The method of claim 11 further comprising the step of comparing the PMPMEase activity in the biological sample to PMPMEase activity in a non-cancerous biological sample.

14. The method of claim 11 wherein the assaying step comprises incubating the biological sample with a PMPMEase substrate and measuring a change in concentration of the substrate or a product known to be produced by PMPMEase from the substrate.

15. The method of claim 14 wherein the substrate is L-N-(4-nitrobenzoyl)-S-trans,trans-farnesyl-cysteine methyl ester (RD-PNB).

16. The method of claim 12 wherein the expression of PMPMEase is determined by an immunological method.

17. The method of claim 12 wherein the expression of PMPMEase is determined by real time-polymerase chain reaction (RT-PCR).

18. A method for monitoring treatment of breast cancer in a subject comprising the steps of collecting a biological sample from the subject and assaying the biological sample for PMPMEase activity.

19. The method of claim 18 further comprising the step of comparing the PMPMEase activity in the biological sample to PMPMEase activity in a non-cancerous biological sample.

20. The method of claim 18 wherein the assaying step comprises incubating the biological sample with a PMPMEase substrate and measuring a change in concentration of the substrate or a product known to be produced by PMPMEase from the substrate.

* * * * *